United States Patent [19]

Takenawa et al.

[11] Patent Number: 4,929,451

[45] Date of Patent: May 29, 1990

[54] PROCESS FOR ELIMINATING DISAGREEABLE ODOR FROM SOYA MILK

[75] Inventors: Seishi Takenawa, Nara; Hideki Takeda, Tenri; Mie Horikoshi, Higashiosaka, all of Japan

[73] Assignee: Fujisawa Pharmaceutical Company, Ltd., Osaka, Japan

[21] Appl. No.: 306,558

[22] Filed: Feb. 6, 1989

[30] Foreign Application Priority Data

Feb. 12, 1988 [JP] Japan ................................. 63-31107

[51] Int. Cl.$^5$ ........................... A23J 1/14; A23L 1/20
[52] U.S. Cl. ........................................ 426/10; 426/46; 426/52; 426/598; 426/634
[58] Field of Search .................... 426/46, 10, 52, 634, 426/598

[56] References Cited

U.S. PATENT DOCUMENTS

| | | | |
|---|---|---|---|
| 3,160,508 | 12/1964 | Scott | 426/10 |
| 3,937,843 | 2/1976 | Osaka et al. | 426/46 |
| 3,966,632 | 6/1976 | Colliopoulos et al. | 426/602 |
| 4,064,277 | 12/1977 | Yokotsuka et al. | 426/598 |
| 4,806,367 | 2/1989 | Kiuchi et al. | 426/46 |

FOREIGN PATENT DOCUMENTS

| | | | |
|---|---|---|---|
| 57-74076 | 5/1982 | Japan . | |
| 57-122775 | 7/1982 | Japan | 426/10 |
| 57-170180 | 10/1982 | Japan | 426/10 |

*Primary Examiner*—Donald E. Czaja
*Assistant Examiner*—Evan Federman
*Attorney, Agent, or Firm*—Oblon, Spivak, McClelland, Maier & Neustadt

[57] ABSTRACT

This invention relates to a process for eliminating disagreeable odors form soya milk whereby soaked soybeans are ground with water whose dissolved oxygen has been decreased by the addition of glucose and glucose oxidase.

6 Claims, No Drawings

PROCESS FOR ELIMINATING DISAGREEABLE ODOR FROM SOYA MILK

This invention relates to a composition eliminating disagreeable odor from soya milk and to a process for preparation of soya milk with an improved flavor, and more particularly to a composition for eliminating disagreeable odor from soya milk containing glucose and glucose oxidase and to a process for preparation of soya milk with an improved flavor which comprises grinding soybean with water whose dissolved oxygen has been substantially decreased or eliminated by addition of glucose and glucose oxidase.

For eliminating disagreeable odors (bean odor and green leguminous odor) from soya milk, it has heretofore been practiced to boil, cook or otherwise heat-treat the raw material soybean and grind the same to provide soya milk or grind the soybean with boiling water. However, these conventional methods have the disadvantage that the heat applied detracts from the gelation potential of the soybean protein.

The intensive and diligent research undertaken for overcoming the above-mentioned problems by the inventors of this invention revealed that soya milk free of disagreeable odors and having an improved flavor can be manufactured by grinding soybean together with water having dissolved oxygen decreased or eliminated by addition of glucose and glucose oxidase (when glucose and glucose oxidase are added to water, the dissolved oxygen in the water is decreased or eliminated by the reaction of the two additives) and, then, processing the same into soya milk in otherwise the routine manner. This finding was followed by further investigation which has resulted in this invention.

Accordingly, an object of this invention is to provide a composition for eliminating disageeable odors from soya milk. Another object of this invention is to provide a process for preparation of disagreeable odors-free soya milk without detracting from gelation potential of the soya protein.

Glucose and glucose oxidase, which are used in accordance with this invention, are both well-known, and glucose oxidase may be of animal origin or vegetable origin or one derived from some microorganism.

The level of addition of glucose to water is optional only if it is not less than 0.02% and for the purpose of decreasing or eliminating dissolved oxygen, the range of 0.02% to 1% (weight %) is generally sufficient. The level of addition of glucose oxidase is not less than 5 units/l (the activity to convert 1.0 $\mu$mol of glucose to gluconic acid in a minute at pH 5.1 and 35° C. is taken as unity; the same applies hereinafter) and generally the range of about 5 to 10,000 units/l is sufficient. Thus, when water containing glucose and glucose oxidase, typically water containing 1% of glucose and 1000 units/l of glucose oxidase, is allowed to stand at 20° C. for about 10 minutes, dissolved oxygen in the water is almost completely eliminated. Therefore, using water whose dissolved oxygen has thus been decreased or eliminated, soybean is ground.

It is also possible to add glucose and glucose oxidase concurrently with water to soybean, and after confirmation that the dissolved oxygen has been decreased or eliminated, start grinding of the soybean.

Moreover, while it is common practice to soak raw soybean in water prior to grinding in the production of soya milk, better results are obtained by soaking soybean in water containing glucose and glucose oxidase and, then, grinding the same with water whose dissolved oxygen has been decreased or eliminated.

The production of soya milk according to this invention is carried out in otherwise the conventional steps (soaking of raw soybean→drain→grinding→go→steaming (boiling)→filtration→soya milk). When the soybean is to be ground with water whose dissolved oxygen has been decreased or eliminated by addition of glucose and glucose oxidase in otherwise the conventional manner, a depression in pH and, hence, a decrease in the extraction yield of soya milk can be prevented by adding a salt, such as sodium carbonate, sodium hydrogen carbonate, sodium citrate or the like, to the ground soybean beforehand. The salt may be added to the go prior to cooking. Furthermore, for removal of hydrogen peroxide, catalase may be used in combination with glucose and glucose oxidase, and the level of addition of catalase to water may generally be in the range of 20 to 40,000 units/l (as to unit, please see the assay method in Test Example 5). In order that the effects of this invention may be better materialized, the production of soya milk can be carried out with the plenum air in the head space of the production system replaced with $N_2$ or $CO_2$ gas.

Furthermore, a still better result is obtained by taking the following step: Thus, after soaked raw soybean is drained, it may be heated in a water bath for a certain time period before carrying out the grinding with water whose dissolved oxygen has been substially eliminated by addition of glucose and glucose oxidase. In this process, however, a decrease in gelation potential of soya milk is unavoidable when the heating temperature for soybean is too high. Therefore, when a heat treatment precedes grinding, the heating temperature should be somewhere between 65° C. and 75° C. in order that the gelation potential of soya milk may be substantially kept intact. If the temperature exceeds the above range, there occurs a significant decrease in the gelation potential of soya milk, while the improving effect of heat treatment on green leguminous odor cannot be achieved when the heating temperature is below the above-mentioned range.

A process for preparation of the disagreeable odors-free soya milk may generally be carried out in the following steps:

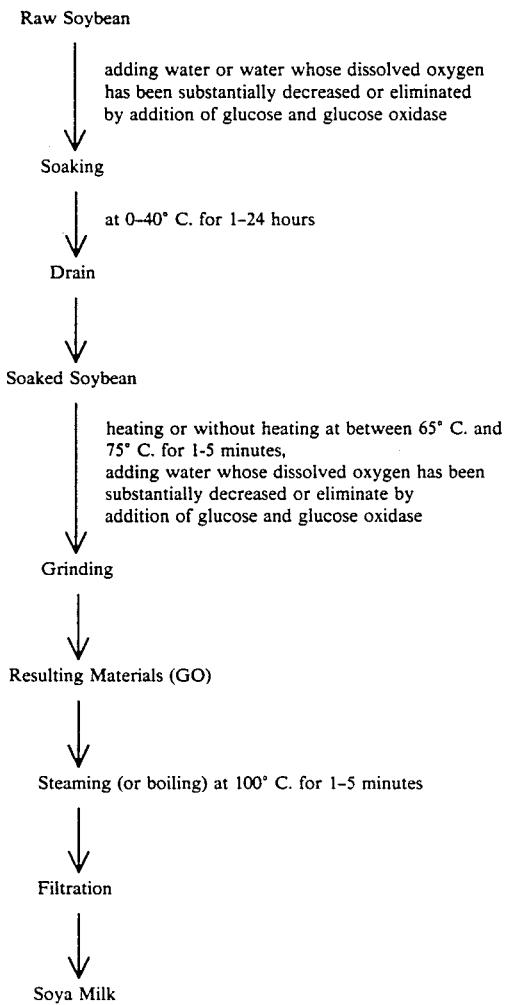

For the composition for eliminating disagreeable odor from soya milk containing glucose and glucose oxidase, the relative amount of glucose and glucose oxidase is 100–300 weight parts of glucose to 1 weight part of glucose oxidase (assuming that its activity is 60 units/mg). Further in case of adding catalase to the composition, the relative amount of the three components is 100–300 weight parts of glucose: 1 weight part of glucose oxidase (assuming that its activity is 60 unites/mg): 1 weight part of catalase (assuming that its activity is 250 units/mg, please see the assay method in Test Example 5).

The soya milk manufactured in accordance with this invention has had disagreeable odors (soybean odor, green leguminous odor) eliminated or decreased and has an improved flavor, and as such can be effectively utilized as an organoleptically improved raw material for the manufacture of soybean curd, dessert foods (yoghurt, ice cream, etc.) or other foods (bread, fish paste, hamburger, etc.).

The following test examples are illustrative of the effects of this invention.

TEST EXAMPLE 1

To 200 g of soybean soaked in water overnight was added 350 ml of one of the waters prepared as below and the mixture was ground in a mixer to give a go. This go was heated by steaming until it attained a temperature of 100° C., at which temperature it was held for a further 3 minutes. The steamed go was immediately filtered through a filter cloth to remove the cake and recover a soya milk. This soya milk was subjected to a sensory test using a panel of 10 tasters. The results (the average scores by 10 panelists) are shown in Table 1. Most of the panelists pointed out a marked improvement in green leguminous odor in the case of the soya milk treated with water containing glucose and glucose oxidase. Furthermore, there was found no definite difference depending on the level of addition of glucose oxidase.

Test groups (water used for grinding)

(1) A solution of 10 g of glucose in 1 of water was allowed to stand at 15° C. overnight.

(2) A solution of 10 g of glucose and 6 units of glucose oxidase in 1 l of water was allowed to stand at 15° C. overnight.

(3) A solution of 10 g of glucose and 60 units of glucose oxidase in 1 l of water was allowed to stand at 15° C. overnight.

(4) A solution of 10 g of glucose and 600 units of glucose oxidase in 1 l of water was allowed to stand at 15° C. overnight.

(5) A solution of 10 g of glucose and 6000 units of glucose oxidase in 1 l of water was allowed to stand at 15° C. overnight.

TABLE 1

|  | Score |
|---|---|
| (1) (Control) | 4.0 |
| (2) | 1.9 |
| (3) | 1.2 |
| (4) | 1.5 |
| (5) | 1.3 |

| Score | Evaluation |
|---|---|
| 0 | No green leguminous odor |
| 1 | Faint green leguminous odor |
| 2 | Slight green leguminous odor (The green leguminous odor is slight but conspicuous) |
| 3 | Intense green leguminous odor |
| 4 | Very intense green leguminous odor |

TEST EXAMPLE 2

Using soybean soaked in water overnight, soya milks were prepared as described below and subjected to a sensory test in the same manner as in Test Example 1. The results are shown in Table 2. Purging the plenum air in the head space of the production system with $N_2$ gas resulted in some improvement in green leguminous odor but the improvement effect was more significant when glucose oxidase was concomitantly used.

Test groups (1) To 200 g of the same soybean as above was added 350 ml of water prepared by dissolving 10 g of glucose in 1 ( of water and allowing it to stand at 15° C. overnight. The mixture was ground in a mixer to prepare a go. This go was steamed until it reached a temperature of 100° C. and held at this temperature for a further 3 minutes, after which it was immediately filtered through a filter cloth to remove the cake and recover a soya milk.

(2) A soya milk was prepared in the same manner as (1) except that the head space air was replaced with $N_2$ gas in the grinding and steaming stages.

(3) A soya milk was prepared in the same manner as (2) except that in lieu of the water prepared by dissolving 10 g of glucose in 1 l of water, the water prepared by dissolving 10 g of glucose and 000 units of glucose oxidase in 1 l of water and allowing the solution to stand at 15° C. overnight was used.

TABLE 2

|  |  | Score |
|---|---|---|
| Test group (Control) | (1) | 3.9 |
| Test group (Control) | (2) | 2.8 |
| Test group | (3) | 1.1 |

TEST EXAMPLE 3

The test soya milks described below were prepared and subjected to the same sensory test as in Test Example 1. The results are shown in Table 3. It is clear that the addition of glucose oxidase to soaking water results in a more remarkable improvement in green leguminous odor.

Test groups (1) To 200 g of soybean soaked in water overnight was added 350 ml of a grinding water prepared by dissolving 10 g of glucose in 1 l of water and allowing the solution to stand at 15° C. overnight and the mixture was ground in a mixer to prepare a go. This go was steamed until it reached 100° C., at which temperature it was further held for 3 minutes. It was immediately filtered through a filter cloth to remove the cake and recover a soya milk. A soya milk was prepared in the same manner as (1) except that the head space plenum air was replaced with $N_2$ gas in the grinding and steaming stages.

(3) A soya milk was prepared in the same manner as (2) except that a grinding water prepared by dissolving 10 g of glucose and 3000 units of glucose oxidase in 1 l of water and allowing the solution to stand at 15° C. overnight was used in lieu of the grinding water (prepared by dissolving 10 g of glucose in 1 ( of water and allowing the solution to stand at 15° C. overnight) used in (2).

(4) A soya milk was prepared in the same manner as (3) except that 200 g of soybean soaked overnight in a soaking water prepared by dissolving 10 g of glucose and 3000 units of glucose oxidase in 1 l of water was used.

TABLE 3

|  |  | Score |
|---|---|---|
| Test group (Control) | (1) | 3.9 |
| (Control) | (2) | 2.8 |
|  | (3) | 1.4 |
|  | (4) | 0.8 |

TEST EXAMPLE 4

Each of the soya milks prepared in Test Example 3 was cooled to 20° C. and, after addition of 0.3% gluconodelta-lactone, heated in a water bath at 80° C. for 30 minutes to give a soybean curd. Although no intergroup difference was found in any of consistency, mouth-feel, taste and other qualities, the soya milk prepared with the use of glucose oxidase showed a marked improvement in green leguminous odor.

TEST EXAMPLE 5

To 200 g of soybean soaked in water overnight was added 350 ml of a grinding water prepared by dissolving 10 g of glucose, 1800 units of glucose oxidase and 8000 units of catalase (the activity to decompose 1.0 $\mu$mole of hydrogen peroxide into water and oxygen in one minute at pH 7.0 and 25° C. is defined as unity) in 1 l of water and allowing the solution at 15° C. overnight and 0.5 g of sodium hydrogen carbonate (anhydrous) and the mixture was ground in a mixer to prepare a go. This go was steamed until it attained a temperature of 100° C. and the heating was further continued for 3 minutes. The cake was immediately separated to give about 450 ml cf soya milk with an improved flavor.

TEST EXAMPLE 6

Soya milks were prepared as mentioned below and subjected to a sensory test in the same manner as in Test Example 1. In addition, each of the soya milks was cooled to 20° C. and after addition of 0.3% of gluconodelta-lactone, heated in a water bath at 90° C. for 40 minutes. The consistency of the resulting soybean curd was measured with a curd meter. The results are shown in Table 4.

The sample subjected to a water bath treatment at 70° C. prior to grinding showed a slight decrease in consistency as compared with the sample not subjected to the treatment but a greater improvement in green leguminous odor. Soybean was soaked overnight in a soaking water prepared by adding 10 g of glucose and 3000 units of glucose oxidase to 1 l of water. A 200 g portion of the soaked soybean was then immersed in a water bath at 70° C. for 2 minutes and drained. To this soybean was added 350 ml of a grinding water prepared by dissolving 10 g of glucose and 3000 units of glucose oxidase in 1 l of water and allowing the solution to stand at 15° C. overnight and the mixture was ground in a mixer to give a go. This go was steamed until it attained a temperature of 100° C., at which temperature it was held for another 3 minutes. The steamed go was immediately filtered through a filter cloth to remove the cake, leaving a soya milk.

(2) A soya milk was prepared in the same manner as Test Group (1) except that raw soybean was soaked overnight in a soaking water prepared by dissolving 10 g of glucose and 3000 units of glucose oxidase in 1 l of water and 200 g of the well-soaked soybean was immersed in a water bath at 85° C. for 2 minutes, at the end of which time it was drained.

(3) A soya milk was prepared in the same manner as Test Group (4) in Test Example 3.

TABLE 4

|  |  | Sensory test score | Curd meter consistency |
|---|---|---|---|
| Test group | (1) | 0.5 | 40 |
|  | (2) | 0.5 | Little gelation |
|  | (3) | 0.9 | 48 |

We claim:
1. A process for preparation of disagreeable odors-free soya milk which comprises
    soaking raw soybean in water,
    draining,
    grinding the soaked soybean with water whose dissolved oxygen has been decreased by addition of glucose and glucose oxidase, steaming the ground soybean, and filtering the resulting materials to obtain disagreeable odors-free soya milk.

2. A process according to claim 1, wherein the grinding is carried out with water whose dissolved oxygen has been decreased by addition of glucose, glucose oxidase and catalase.

3. In a process for eliminating disagreeable odors from soya milk, a soaked soybean is ground with water whose dissolved oxygen has been decreased by addition of glucose and glucose oxidase.

4. A process according to claim 3, wherein the soaked soybean is ground with water whose dissolved oxygen has been decreased by addition of glucose, glucose oxidase and catalase.

5. A process according to claim 1, wherein the relative amount of glucose and glucose oxidase is 100–300 weight parts of glucose to 1 weight part of glucose oxidase of an activity of 60 units/mg.

6. A process according to claim 2 or 4, wherein the relative amount of glucose, glucose oxidase and catalase is 100–300 weight parts of glucose: 1 weight part of glucose oxidase of an activity of 60 units/mg: 1 weight part of catalase of an activity of 250 units/mg.

* * * * *